United States Patent [19]  [11] 3,943,145
Gagneux et al.  [45] Mar. 9, 1976

[54] 6-PHENYL-4H-V-TRIAZOLO[1,5-A][1,4]BENZODIAZEPINES

[75] Inventors: André Gagneux, Basel; Roland Heckendorn, Arlesheim; René Meier, Buus, all of Switzerland

[73] Assignee: Ciba-Geigy Corporation, Ardsley, N.Y.

[22] Filed: Dec. 20, 1973

[21] Appl. No.: 427,167

[30] Foreign Application Priority Data
 Dec. 29, 1972 Switzerland............ 19079/72

[52] U.S. Cl. 260/308 A; 260/247.5 EP; 260/268 TR; 260/293.59; 260/349; 260/570 AB; 424/248; 424/250; 424/267; 424/269
[51] Int. Cl.²......................... C07D 487/04
[58] Field of Search............ 260/308 R, 308 A

[56] References Cited
UNITED STATES PATENTS
3,703,525 11/1972 Tawada et al.............. 260/308 R Primary Examiner—Alton D. Rollins
Attorney, Agent, or Firm—Joseph G. Kolodny; John J. Maitner; Theodore O. Groeger

[57] ABSTRACT

Compounds of the class of 6-phenyl-4H-v-triazolo[1,5-a][1,4] benzodiazepines, which in the 3-position are unsubstituted or substituted, particularly by a carbamoyl group or a substituted carbamoyl group, their 5-oxides and their pharmaceutically acceptable acid addition salts have valuable pharmacological properties and are active ingredients for therapeutic compositions. In particular, these new compounds have an anticonvulsive and anti-aggressive action. Specific embodiments are N,N-dimethyl-6-phenyl-8-chloro-4H-v-triazolo[1,5-a][1,4]benzodiazepine-3-carboxamide and N,N-dimethyl-6-(o-fluorophenyl)-8-chloro-4H-v-triazolo[1,5-a][1,4]benzodiazepine-3-carboxamide.

23 Claims, No Drawings

6-PHENYL-4H-V-TRIAZOLO[1,5-A][1,4]BENZODIAZEPINES

The present invention relates to new diazepine derivatives, therapeutic compositions which contain the new compounds, and a method for the treatment states of strain and agitation.

The diazepine derivatives according to the invention correspond to the formula I

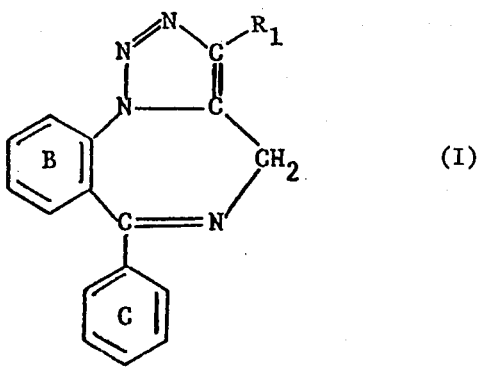

in which
R₁ represents hydrogen, lower alkyl, lower hydroxyalkyl, etherified lower hydroxyalkyl, esterified lower hydroxyalkyl, lower aminoalkyl, monosubstituted lower aminoalkyl, disubstituted lower aminoakyl, formyl, di-(lower-alkoxy)methyl, carboxyl, (lower alkoxy)-carbonyl, cyano, carbamoyl monosubstituted carbamoyl or disubstituted carbamoyl and
the rings B and C are unsubstituted or substituted independently of each other by halogen up to atomic number 35, alkyl or alkoxy each having 1 to 7 carbon atoms, trifluoromethyl or nitro.

The subject of the invention also comprises the 5-oxides and the pharmaceutically acceptable addition salts of the compounds of the general formula I with inorganic and organic acids.

In the definition of R¹, lower groups are understood as groups with 1 to 7 and preferably with 1 to 4 carbon atoms. R₁ as lower alkyl is, for example, ethyl, propyl, isopropyl, butyl, isobutyl, pentyl, hexyl or heptyl and above all methyl. Optionally etherified or esterified lower hydroxyalkyl for example, 1-hydroxyethyl-,, 2-hydroxyethyl, 1-, 2- and 3-hydroxypropyl, 1-hydroxy-1-methylethyl, 1- and 2-hydroxybutyl, 1-hydroxypentyl, 1-hydroxyhexyl or 1-hydroxyl-heptyl and preferably hydroxymethyl, (lower alkoxy)-(lower alkyl), such as methoxymethyl, ethoxymethyl, isopropoxymethyl, butoxymethyl, 2-methoxyethyl, 2-ethoxyethyl, 2-propoxyethyl or 2-butoxyethyl, aralkoxy-(lower alkoxy), such as benzyloxymethyl, (p-methoxybenzyloxy)-methyl and 2-benzyloxyethyl, or (lower alkanoyloxy)-(lower alkyl), such as acetoxymethyl, propionyloxymethyl, butyryloxymethyl, valeryloxymethyl, pivaloyloxymethyl, hexanoyloxymethyl, heptanoyloxymethyl, 2-acetoxyethyl or 2-butyryloxyethyl.

As an optionally monosubstituted or disubstituted lower aminoalkyl, R₁ is in particular a group of the general formula Ia

in which A represents alkylene with 1 to 3 carbon atoms, such as ethylene, propylene, trimethylene and above all methylene and R₂ and R₃ independently of each other represent hydrogen, alkyl with 1 to 7 carbon atoms, hydroxyalkyl with 2 to 7 carbon atoms, dialkylaminoalkyl with a total of 4 to 7 carbon atoms or aralkyl groups with 7 to 9 carbon atoms, or R₂ and R₃ are lower alkyl groups linked to one another directly or in the β- or ε-position also via an oxygen atom, imino, lower alkylimino or hydroxyalkylimino with at most 4 carbon atoms, to give a divalent radical with a total of at most 10 carbon atoms.

R₂ and R₃, as alkyl with 1 to 7 carbon atoms, are, for example, propyl, isopropyl, butyl, isobutyl, pentyl, isopentyl, hexyl or heptyl and particularly groups or ethyl which together with hydrogen are the preferred embodiments of R₂ and R₃. As hydroxyalkyl with 2 to 7 carbon atoms R₂ and R₃ are, for example, 2-hydroxypropyl, 3-hydropypropyl, 2-hydroxybutyl, 3-hydroxybutyl, 2-hydroxy-1-methyl-propyl, 2-hydroxypentyl, 2-hydroxyhexyl or 2-hydroxyheptyl and especially 2-hydroxyethyl, as dialkylaminoalkyl with 4 to 7 carbon atoms they are, for example, 2-(dimethylamino)-ethyl, 2-(dimethylamino)-propyl, 3-(dimethylamino)-propyl, 2-(diethylamino)-ethyl or 3-(diethylamino)-propyl, and as aralkyl with 7 to 9 carbon atoms they are, for example, benzyl, phenethyl, α-, o-, m- or p-methylbenzyl, 3-phenylpropyl or α-methylphenethyl. With the exception of lower alkyl, the abovementioned groups are preferably only present as R₂, that is to say only present once, together with a hydrogen atom or lower alkyl as R₃.

Alkyl groups R₂ and R₃ linked to one another in the manner defined above for example form, together with the adjoining nitrogen atom, that is to say as the grouping NR₂R₃, the 1-aziridinyl, 1-azetidinyl, 1-pyrrolidinyl, piperidino, hexahydro-1H-azepin-1-yl, morpholino, 1-piperazinyl or hexahydro-1H-1,4-diazepin-1-yl group. The two latter groups can be substituted in the 4-position, that is to say in the imino group, for example by an ethyl, propyl, isopropyl, butyl, isobutyl, 2-hydroxypropyl, 3-hydroxypropyl or 3-hydroxybutyl group and especially a methyl group or a 2-hydroxyethyl group, whilst all the abovementioned rings can additionally be substituted at carbon atoms by ethyl, propyl or especially methyl groups. As examples of C-alkyl-substituted or C- and N-substituted radicals NR₂R₃ there may be mentioned the 2-methyl-1-aziridinyl, 3,3-dimethyl-1-azetidinyl, 2,5-dimethyl-1-pyrrolidinyl, 2-methyl-, 3-methyl- and 4-methyl-piperidino, 2,6-dimethyl-piperidino, 2,4,6-trimethyl-piperidino, 2,2,6,6-tetramethyl-piperidino, 2,5-dimethyl-1-piperazinyl, 2,4,5-trimethyl-1-piperazinyl, 2,4,6-trimethyl-1-piperazinyl and 3,4,5-trimethyl-1-piperazinyl group. The preferred groups of this series are 1-pyrrolidinyl-, piperidine and 4-methyl-1-piperazinyl.

As di-(lower alkoxy)-methyl R₁ is in particular dimethoxymethyl or diethoxymethyl. As (lower alkoxy)-carbonyl, R₁ is, for example, propoxy carbonyl, isopropoxy carbonyl, butoxycarbonyl, isobutoxycarbonyl, tert.butoxycarbonyl, pentyloxycarbonyl, isopentyloxycarbonyl, hexyloxycarbonyl or heptyloxycarbonyl but preferably ethoxycarbonyl and above all methoxycarbonyl.

An optionally monosubstituted or disubstituted carbamoyl group R₁ is in particular a group of the formula Ib

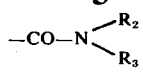
(Ib)

in which $R_2$ and $R_3$ have the meaning indicated under the formula Ia. Here again, $R_2$ and $R_3$ or the grouping $NR_2R_3$ can be the groups already mentioned earlier.

As substituents of the rings B and C, halogen atoms are understood as fluorine, chlorine or bromine atoms, whilst alkyl groups or alkoxy groups with 1 to 7 carbon atoms are, for example, methyl, ethyl, propyl, isopropyl, butyl, isobutyl, tert.butyl, pentyl, isopentyl, 1,1-dimethylpropyl, 2,2-dimethylpropyl, hexyl, isohexyl or heptyl or methoxy, ethoxy, propoxy, isopropoxy, butoxy, isobutoxy, pentyloxy, isopentyloxy, 2,2-dimethylpropoxy, hexyloxy, isohexyloxy or heptyloxy. A substituent of the ring B is preferably fluorine, bromine, trifluoromethyl, especially nitro and above all chlorine. Such a substituent is, in particular, in the 8-position. The ring C is preferably unsubstituted or substituted in any desired position by fluorine, chlorine, bromine, the trifluoromethyl group or the nitro group, but especially by fluorine or chlorine in the o-position.

The compounds of the formula I, their 5-oxides and their addition salts with inorganic and organic acids possess valuable pharmacological properties. They have a damping effect on the central nervous system, and in particular an anti-convulsive, anti-aggressive and narcosis-potentiating action. The anti-convulsive activity can be established, for example, in the pentetrazole cramp test on mice with doses from approx. 0.026 mg/kg, administered orally, and in the strychnine cramp test on mice with doses from approx. 0.5 mg/kg administered orally. The damping effect on the central nervous system, especially the anti-convulsive properties and further types of actions which can be measured by suitable standard tests [compare W. Theobald and H. A. Kunz, Arzneimittelforsch. 13, 122 (1963) and W. Theobald et al., Arzneimittelforsch. 17, 561 (1967)], characterise the compounds of the general formula I, their 5-oxides and their pharmaceutically acceptable addition salts with inorganic and organic acids, as active substances for psychosedatives (tranquillisers) and anti-convulsives which can be used, for example, for the treatment of states of strain and agitation and for the treatment of epilepsy.

Compounds of particular importance are those of the general formula I in which $R_1$ is hydrogen or a group of the general formula Ib, in which $R_2$ and $R_3$ have the meaning indicated earlier, but preferably denote hydrogen and/or lower alkyl, especially methyl or ethyl, or together with the adjoining nitrogen atom denote the 1-pyrrolidinyl, piperidino or 4-methyl-1-piperazinyl group. Compounds of the general formula I, in which $R_1$ is hydroxymethyl or, as a radical of the general formula Ia, aminomethyl, are particularly valuable, above all because of their ready accessibility and diverse applicability as intermediate products. Also especially valuable as intermediates are compounds of the formula I, wherein $R_1$ is the formyl or carboxy group or a lower alkoxycarbonyl group, preferably the methoxycarbonyl group. Furthermore, quite generally, and also within the abovementioned preferred groups of compounds, those in which the ring B is unsubstituted or preferably substituted in the 8-position by halogen of atomic number up to 35, nitro or trifluoromethyl and the ring C is either unsubstituted or substituted by one of the substituents mentioned for the ring B are of particular interest. Within these groups of compounds, particularly important compounds are, on the one hand, those with one of the abovementioned substituents, especially trifluoromethyl, preferably nitro and above all chlorine, in the 8-position in ring B, and, on the other hand, those with a ring C which is unsubstituted or substituted by fluorine or chlorine in the o-position. Particularly valuable compounds are those which combine the abovementioned substitution characteristics of the rings B and C and at the same time contain, as $R_1$, a group of the general formula Ib, in which $R_2$ and $R_3$ denote hydrogen and/or methyl or ethyl, such as N,N-dimethyl-6-phenyl-8-chloro-4H-v-triazolo[1,5-a][1,4]benzodiazepine-3-carboxamide and N,N-dimethyl-6-(o-fluorophenyl)-8-chloro-4H-v-triazolo [1,5-a][1,4]benzodiazepine-3-carboxamide.

According to a first process according to the invention, compounds of the general formula I, their 5-oxides and their acid addition salts are manufactured by condensing a compound of the general formula II,

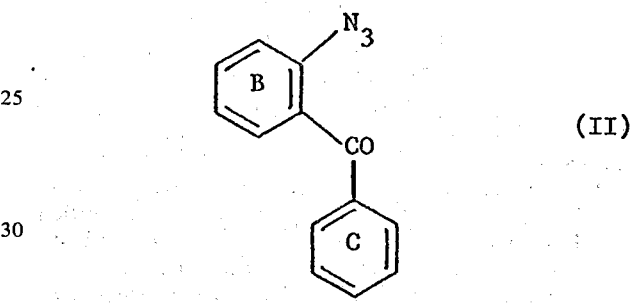

in which the rings B and C can be substituted as indicated under the formula I, with a compound of the general formula III

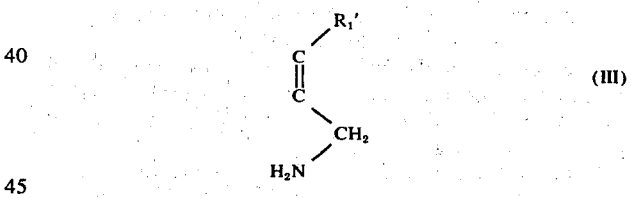

in which $R_1'$ has the meaning indicated for $R_1$ under the formula I, with the exception of esterified lower hydroxyalkyl groups, the formyl group, the carboxyl group and lower alkoxycarbonyl groups, if desired, esterifying a reaction product in which $R_1'$ is a lower hydroxyalkyl group, or oxidising a reaction product in which $R_1'$ is the hydroxymethyl group, to give the corresponding aldehyde or to give the corresponding carboxylic acid, if desired converting the resulting aldehyde, by reaction with a lower alkanol in the presence of an alkali metal cyanide and manganese dioxide, or converting the resulting carboxylic acid by customary esterification processes, into a corresponding compound with a lower alkoxy group $R_1$ and/or, if desired, oxidising a resulting compound of the general formula I to its 5-oxide or, if desired, converting a resulting compound of the general formula I to an acid addition salt with an inorganic or organic acid.

The condensation according to the invention is carried out in the presence or absence of a solvent and preferably in the presence of a condensation agent. Suitable solvents are hydrocarbons, such as benzene or toluene, chlorinated hydrocarbons, such as carbon tetrachloride, or lower alkanols, for example methanol or ethanol, or tertiary organic bases, such as pyridine. Suitable condensation agents are hydrochlorides of inorganic or organic bases, for example ammonium chloride or pyridine hydrochloride, and also hydrogen halides, such as hydrogen chloride, or Lewis acids, such as titanium tetrachloride. If the starting substance of the general formula III is employed as the hydrochloride, it is possible also to add, as the condensation agent, the free base, especially pyridine, instead of the hydrochloride of a tertiary organic base. The reaction temperature is preferably about 0° to 120°C.

The esterification of reaction products which contain a lower hydroxyalkyl group as the group $R_1'$ is carried out in the customary manner. For example, it is effected by reaction with carboxylic acid halides or carboxylic acid anhydrides, especially with lower alkanoyl chlorides or bromides or with corresponding anhydrides, in the presence of an acid-binding agent, for example of a tertiary organic base, such as pyridine or triethylamine, at temperatures between approx. 0° and 100°C, in a solvent. Examples of suitable solvents are hydrocarbons, such as benzene or toluene, halogenated hydrocarbons, such as carbon tetrachloride or chloroform, or an excess of the tertiary organic base employed as an acid-binding agent.

The oxidation of reaction products whereof the radical $R_1'$ is a hydroxymethyl group, to corresponding aldehydes is preferably carried out by means of manganese dioxide in an inert organic solvent, such as, for example, benzene, at temperatures between approx. 60° and 100°C or at the boiling point of the solvent employed. The oxidation can furthermore also be effected, for example, by means of dimethylsulphoxide in the presence of dicyclohexylcarbodiimide and phosphoric acid. The oxidation of reaction products with a hydroxymethyl group $R_1'$ to give the corresponding carboxylic acids is effected, for example, by means of chromium trioxide in an acid medium. It is also possible to use, as starting substances, the aldehydes manufactured according to the abovementioned process, that is to say to effect the conversion of the hydroxymethyl group $R_1'$ into the carboxyl group in two stages. The 3-(hydroxymethyl) compounds falling under the general formula I and used for the abovementioned oxidations can not only be manufactured by direct reaction of compounds of the general formula II with the 4-amino-2-butin-1-ol falling under the general formula III but also from the 3-(aminomethyl) compounds, obtained analogously using 2-butine-1,4-diamine, by reaction with nitrous acid or with an alkali metal nitrite and very dilute sulphuric acid.

The conversion of aldehydes falling under the general formula I into lower alkyl esters of the corresponding carboxylic acids is effected, for example, in a reaction medium of the alkanol desired as the ester component, with addition of a major excess relative to the aldehyde employed, for example of an approx. 5-fold molar amount, of alkali metal cyanide, especially sodium cyanide, and of an even greater excess, for example an approx. 20-fold molar amount, of manganese dioxide and a little glacial acetic acid, at room temperature or slightly elevated temperatures of up to approx. 60°C. To esterify the carboxylic acids falling under the general formula I by customary methods, such carboxylic acids are, for example, warmed or boiled in the lower alkanols desired as the ester component, which are saturated with hydrogen chloride, or the carboxylic acids are first converted, for example by means of excess thionyl chloride, into their acid chlorides or their mixtures with the corresponding hydrochlorides, and these are reacted with the lower alkanols desired as the ester component.

The conversion of the resulting compounds of the general formula I into their 5-oxides or into their acid addition salts is explained in more detail below.

The starting materials of the general formula II are manufactured, for example, starting from corresponding 2-amino-benzophenones which are substituted according to the definition in the rings B and C. Such compounds are described in the literature, for example, 2-amino-5-chloro-benzophenone [compare F. D. Chattaway, J. Chem. Soc. 85, 340 (1904)], 2-amino-2',5-dichloro-benzophenone [compare L. H. Sternback et al., J. Org. Chem. 26,4448 (1961)] and 2-amino-5-chloro-2'-benzophenone [compare L. H. Sternbach et al., J. Org. Chem. 27, 3781 (1962)]. Further compounds of this type can be manufactured analogously. These 2-amino-benzophenone derivatives are diazotised, for example with sodium nitrite in acid solution, for example in a mixture of acetic acid and hydrochloric acid, a base, for example, sodium acetate trihydrate, is subsequently added to the resulting diazonium salt solution, and the product is reacted with an azide, for example sodium azide, to give azido-benzophenones of the general formula II.

Amongst the starting materials of the general formula III, some are known and others can be manufactured analogously to the known compounds, see, for example, A. Marszak-Fleury, Compt. rend. 241, 808 (1955) and further references.

According to a second process, the compounds falling under the general formula I, which contain the group of the general formula Ib as $R_1$, their 5-oxides and their acid addition salts are manufactured by reacting a carboxylic acid of the general formula IV,

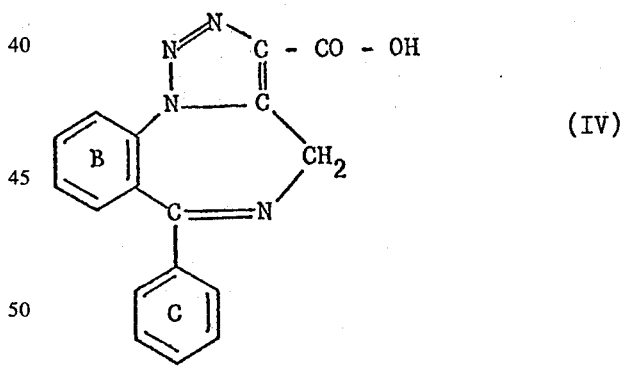

(IV)

in which the rings B and C can be substituted as indicated under the formula I, a reactive functional derivative of such a carboxylic acid or the 5-oxide of such a compound, with a compound of the general formula V

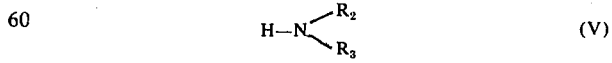

(V)

in which $R_2$ and $R_3$ have the meaning indicated under the formula Ia, or with a reactive functional derivative of such a compound, and, if desired, oxidising the resulting reaction product to its 5-oxide or, if desired, converting it into an addition salt with an inorganic or organic acid. To carry out this process, for example, a carboxylic acid of the formula IV is reacted with a compound of the general formula V in the presence of a carbodiimide such as, for example, dicyclohexylcarbodiimide, in an inert solvent such as, for example, tetrahydrofurane. Lower alkyl esters such as, for example, the methyl esters or ethyl esters of the carboxylic acids of the general formula IV, can be reacted with compounds of the general formula V, even in the cold or if necessary with warming, and optionally in a closed vessel, to give the corresponding amides of the general formula I. Furthermore it is also possible to convert amides which already fall under the general formula I into other amides falling under the general formula I by heating with compounds of the general formula V.

Further suitable reactive functional derivatives of carboxylic acids of he general formula IV are the halides, especially the chlorides, and the ahydrides, especially the mixed anhydrides with carbonic acid half-esters. These functional derivatives are reacted with a compound of the general formula V, preferably in the presence of an acid-binding agent, for example of a strong tertiary organic base, such as triethylamine, N-ethyldiisopropylamine, pyridine or s-colidine, which can, in excess, also serve as the reaction medium, or in the presence of an excess of the reactant of the general formula V, in the presence or absence of an inert organic solvent, such as, for example, dioxane, tetrahydrofurane, benzene or dimethylformamide. Further possible derivatives of the carboxylic acids of the general formula IV are, for example, their p-nitro-phenyl esters and cyanomethyl esters, which are reacted with compounds of the general formula V in inert organic solvents, if necessary with warming. The 1-imidazolides of the carboxylic acids of the general formula IV are reacted under analogous conditions with compounds of the general formula V.

As reactive functional derivatives of compounds of the general formula V which can be reacted directly with acids of the general formula IV there may be mentioned the isocyanates and isothiocyanates derived from compounds of the general formula V with a hydrogen atom as $R_3$. These isocyanates and isothiocyanates are heated with the acids of the general formula IV until the equimolar amount of carbon dioxide or carbon oxysulphide has been liberated. The reactions with isocyanates and isothiocyanates can be carried out in the presence or absence of an inert organic solvent of sufficiently high boiling point or boiling range. As further reactive functional derivatives of compounds of the general formula V with a hydrogen atom as $R_3$ there should also be mentioned the N-trimethylsilyl derivatives obtainable by reaction of these amines with trimethylsilyl chloride in inert, anhydrous organic solvents, which derivatives react with reactive functional derivatives of the acids of the general formula IV in inert organic solvents to give N-trimethylsilyl derivatives of amides falling under the general formula I, from which the desired amides are produced on decomposition with water or lower alkanols.

As functional derivatives of compounds of the general formula V in which neither $R_2$ nor $R_3$ is a hydrogen atom, their N-chlorocarbonyl derivatives, for example, are reacted with salts, for example alkali metal salts, of carboxylic acids of the general formula IV in the presence or absence of inert organic solvents and the reaction mixture is heated until the equimolar amount of carbon dioxide has been liberated from the carboxylic acid/carbamic acid anhydrides formed first. It is also possible to derive, from compounds of the general formula V with radicals $R_2$ and $R_3$ different from hydrogen, sulphurous acid monoalkyl ester/amides and phosphorous acid o-phenylenediester/amides which on reaction with carboxylic acids of the general formula IV in organic solvents such as, for example, pyridine, dioxane or diethylformamide or benzene, give the desired amides embraced by the general formula I.

The conversion of the resulting compounds of the general formula I into their 5-oxides or into their acid addition salts is explained in more detail below.

The carboxylic acids of the general formula IV required as starting materials fall under the general formula I. The manufacture of these acids, and all functional derivatives, such as their lower alkyl esters and their acid chlorides, by the first-mentioned process for the manufacture of the compounds of the general formula I, and secondary reactions, has already been described above. Large numbers of starting materials of the general formula V are known.

According to a third process, the compounds of the general formula I which contain the group of the general formula Ib as $R_1$, their 5-oxides and their acid addition salts are again manufactured, by reacting an aldehyde of the general formula VI

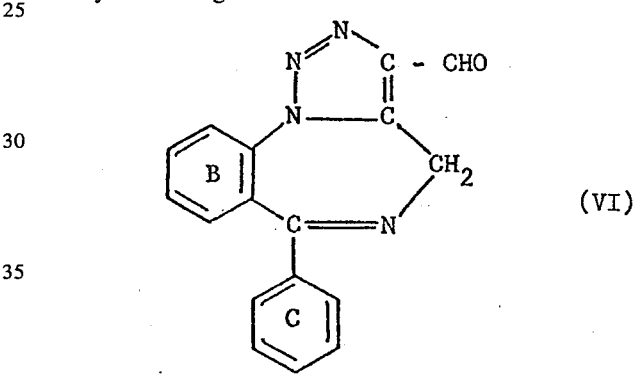

(VI)

in which the rings B and C can be substituted as indicated under the formula I, with a compound of the general formula V indicated earlier, in which $R_2$ and $R_3$ have the meaning indicated under the formula Ia, in the presence of an alkali metal cyanide and a selective oxidising agent, and oxidising the resulting reaction product, if desired, to its 5-oxide, or, if desired, converting it into an addition salt with an inorganic or organic acid. The alkali metal cyanide used is, for example, potassium cyanide and especially sodium cyanide. By selective oxidising agents there are to be understood those which, under the reaction conditions, do not attack the aldehyde group of the starting material of the formula VI but are able to oxidise the hydroxymethylene group of the cyanohydrin formed as an intermediate, to the carbonyl group. A suitable oxidising agent is manganese dioxide, above all in the active form described by J. Attenburrow et al., J. Chem. Soc. 1952, 1104. The reactions with manganese dioxide are preferably carried out in isopropanol or some other lower secondary alkanol to which a further organic solvent which is inert under the reaction conditions, preferably a solvent in which the starting materials of the general formula VI dissolve readily, such as, for example, dioxane, can be added, in the cold, for example between −10° and +10°C, preferably at about 0°C. For example, relative to the compound of the general formula VI a major excess of the compound of the general formula V and of the alkali metal cyanide is employed, for example an approx. 5-fold molar amount of the latter and an even greater excess, for example an approx. 20-fold molar amount, of manganese dioxide, the reaction time being 2 to 6 hours and preferably approx. 4 hours.

The conversion of the resulting compounds of the general formula I into their 5-oxides or into their acid addition salts is explained in more detail below.

The aldehydes of the general formula VI required as starting materials fall under the general formula I. Their manufacture can be effected in accordance with the first-mentioned process for the manufacture of the compounds of the general formula I, including a secondary reaction, that is to say by reaction of 2-azido-benzophenones of the general formula II with 4-amino-2-butin-1-ol and gentle oxidation of the resulting hydroxymethyl compounds, preferably by means of manganese dioxide.

According to a fourth process according to the invention, compounds of the general formula I in which $R_1$ denotes hydrogen, their 5-oxides and their acid addition salts are manufactured by dehydrogenating a compound of the general formula VII

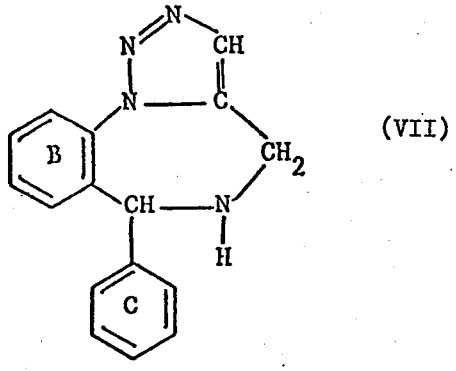

(VII)

in which the rings B and C can be substituted as indicated in connection with the general formula I, if necessary isomerising the corresponding compound of the general formula VIII

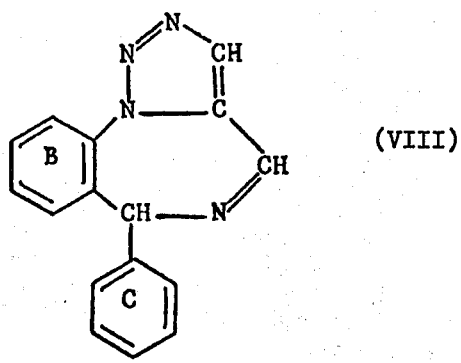

(VIII)

which is produced in addition to the compound of the general formula I, so as to give the compound of the general formula I, the isomerization being carried out in the mixture with the compound of the general formula I or after isolation from this mixture, and, if desired, oxidising the resulting compound of the general formula I to its 5-oxide or converting it into an addition salt with an inorganic or organic acid.

Examples of dehydrogenating agents which can be used in the reaction according to the invention are readily reducible metal oxides, such as chromium-(III) oxide, silver oxide and especially selenium dioxide and manganese dioxide, easily reducible salts, such as iron-(III) Salts, for example iron-(III) chloride, sodium hypochlorite or sodium hypobromite and especially lead tetraacetate, sodium dichromate dihydrate and also halogens, for example chlorine or bromine, as well as quinones, for example 2,3,5,6-tetrachloro-1,4-benzoquinone (chloranil) 3,4,5,6-tetrachloro-1,2-benzoquinone or 2,3-dichloro-5,6-dicyano-1,4-benzoquinone. The dehydrogenating agents are preferably employed in solution or as a finely divided suspension employed in solution of the starting material of the general formula VII. Exampls of inert solvents used are lower alkanoic acids, such as acetic acid, in which, preferably, chromium-(III) oxide, bromine, sodium dichromate dihydrate or lead tetraacetate are employed; also lower alkanols, such as methanol or ethanol, in which bromine in the presence of suitable alkali metal alkanolates, for example sodium methylate, or of sodium hydroxide or potassium hydroxide, is employed; hydrocarbons, such as benzene, toluene or xylene, in which, for example, hydrated manganese dioxide is suspended; tertiary organic bases, for example pyridine, in which, preferably, selenium dioxide is dispersed, or halogenated hydrocarbons, such as methylene chloride or chloroform, in which, for example, lead tetraacetate is employed. Instead of the solvents mentioned, it is also possible to employ mixtures of such solvents, or the solvents mentioned can be used as a mixture with water, in a one-phase or two-phase system. The reaction temperatures are approx. 0° to 150°C.

The conversion of the resulting compounds of the general formula I into their 5-oxides or into their acid addition salts is explained in more detail below.

The starting materials of the general formula VII can be manufactured starting from azido-benzophenones of the general formula II. These are first reacted with hydroxylamine, which is preferably liberated in situ from the hydrochloride by means of a tertiary organic base, to give their 5-oximes. In this reaction, the tertiary organic base used is, for example, pyridine, preferably in an inert solvent, such as ethanol. The resulting oximes are caused to undergo an addition reaction with an acetylenedicarboxylic acid diester, preferably with acetylenedicarboxylic acid dimethyl ester in dioxane, giving 1-[2-(α-hydroxyimino-benzyl)-phenyl]-1H-v-triazole-4,5-dicarboxylic acid dimethyl esters which ca be substituted in the phenyl radical and in the benzyl radical in the manner indicated for the ring B and the ring C, respectively, under the fromula I. These addition products can be reduced, for example catalytically with hydrogen in the presence of palladium on charcoal, in methanol, to give corresponding 1-[2-(α-amino-benzyl)phenyl]-1H-v-triazole-4,5-dicarboxylic acid dimethyl esters, whch are cyclised, preferably by heating in vacuo, to give the corresponding 6-phenyl-5,6-dihydro-4-oxo-4H-v-triazolo[1,5-a][1,4]benzodiazepine-3-carboxylic acid methyl esters. These cyclisation products are hydrolysed with an inorganic base, for example with sodium hydroxide or potassium hydroxide, in a solvent, for example in N,N-dimethylformamide, to give the corresponding free carboxylic acids. The latter can be decarboxylated, preferably by heating in a solvent, such as, for example, quinoline, to give compounds of the general formula VIIa

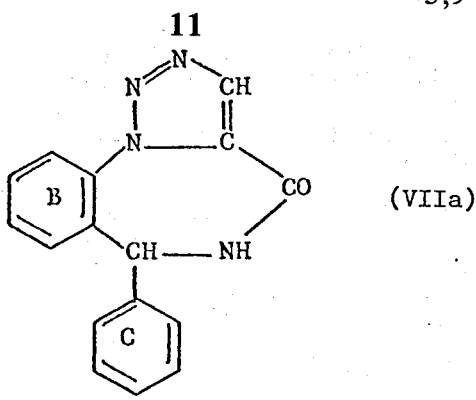 (VIIa)

in which the rings B and C can be substituted as indicated under the formula I. These lactams can be reduced with the aid of a complex metal hydride, for example with lithium aluminium hydride, preferably in ether.

The oxidation to the corresponding 5-oxides which optionally follows the processes, according to the invention, for the manufacture of the compounds of the formula I, is preferably effected by means of hydrogen peroxide or with peroxy-acids at a temperature of approx. 0° to 70°C. Suitable peroxy-acids are, for example, peroxyacetic acid or peroxybenzoic acids, such as peroxybenzoic acid or especially m-chloroperoxybenzoic acid. The oxidising agents are preferably employed in a solvent, for example peroxyacetic acid in acetic acid and peroxybenzoic acids in halogenated hydrocarbons, such as methylene chloride or chloroform.

The compounds of the general formula I obtained according to the process of the invention are converted, if desired, in the usual manner into their addition salts with inorganic and organic acids. For example, a solution of the compound of the general formula I in an organic solvent is treated with the acid desired as the salt component. Preferably, organic solvents in which the resulting salt is sparingly soluble is chosen for the reaction so that the salt can be separated off by filtration. Examples of such solvents are methanol, ether, acetone, methyl ethyl ketone, acetone/ether, acetone/ethanol, methanol/ether or ethanol/ether.

For use as medicines it it possible to employ, instead of free bases, pharmaceutically tolerable acid addition salts, that is to say salts with acids of which the anions are not toxic at the dosages in question. Furthermore it is of advantage if the salts to be used as medicines are readily crystallisable and non-hygroscopic or only slightly hygroscopic. To form salts with compounds of the general formula I it is possible to use, for example, hydrochloric acid, hydrobromic acid, sulphuric acid, phosphoric acid, perchloric acid, methanesulphonic acid, ethanesulphonic acid, 2-hydroxyethanesulphonic acid or citric acid and, especially in the case of compounds of the general formula I in which $R_1$ denotes a group of the general formula Ia, also acetic acid, lactic acid, succinic acid, fumaric acid, maleic acid, malic acid, tartaric acid, benzoic acid, salicylic acid, phenylacetic acid, mandelic acid or embonic acid.

The compounds of the general formula I and their 5-oxides and their pharmaceutically acceptable acid addition salts are preferably administered perorally or rectally but pharmaceutically acceptable acid addition salts can also be administered parenterally as aqueous solutions. The dosage depends on the method of administration, the species, the age and the individual condition. The daily doses vary between 0.01 and 1 mg/kg for warm-blooded animals. Suitable unit dosage forms, such as dragees, tablets or suppositories, preferably contain 0.25–25 mg of an active substance according to the invention, that is to say of a compound of the general formula I, its 5-oxide or a pharmaceutically acceptable acid addition salt of the former. To produce these unit dosage forms, the active substance is combined with solid pulverulent carriers, such as lactose, sucrose, sorbitol and mannitol; starches, such as potato starch, corn starch or amylopectine and also laminaria powder or citrus pulp powder; cellulose derivatives or gelatine, optionally with the addition of lubricants, such as magnesium stearate or calcium stearate or polyethylene glycols, to give tablets or dragee cores. The latter are coated with, for example, concentrated sugar solutions which can additionally contain, for example, gum arabic, talc and/or titanium dioxide, or with a lacquer dissolved in readily volatile organic solvents or solvent mixtures. Dyestuffs can be added to these coatings, for example to characterise different doses of active substance. Further suitable oral unit dosage forms are gelatine push-fit capsules and soft sealed capsules of gelatine and a plasticiser, such as glycerine. The former preferably contain the active substance as granules mixed with lubricants, such as talc or magnesium stearate, and optionally stabilisers, such as sodium metabisulphite or ascorbic acid.

The instructions which follow are intended to explain the manufacture of tablets, dragees and suppositories in more detail:

a. 25.0 G of N,N-dimethyl-6-phenyl-8-chloro-4H-s-triazolo[4,3-a][1,4]benzodiazepine-3-carboxamide are mixed with 500 g of lactose and 292 g of potato starch and the mixture is moistened with an alcoholic solution of 8 g of gelatine and granulated through a sieve. After drying, 60 g of potato starch, 60 g of talc, 10 g of magnesium stearate and 20 g of highly disperse silicon dioxide are added and the mixture is pressed to give 10,000 tablets each weighing 102.5 mg and containing 2.5 mg of active substance, which can, if desired, be provided with breaking grooves for fine adjustment of the dosage.

b. 0.50 G of N,N-dimethyl-6-(o-fluorophenyl)-8-chloro-4H-s-triazolo[4,3-a][1,4]benzodiazepine-3-carboxamide are well mixed with 16 g of corn starch and 6 g of highly disperse silicon dioxide. The mixture is moistened with a solution of 2 g of stearic acid, 6 g of ethyl cellulose and 6 g of stearin in approx. 70 ml of isopropyl alcohol and granulated through a sieve III (Ph.Helv. V). The granules are dried for approx. 14 hours and then forced through a III–IIIa sieve. They are then mixed with 16 g of corn starch, 16 g of talc and 2 g of magnesium stearate and pressed to give 1,000 dragee cores. These are coated with a concentrated syrup of 2 g of shellac, 7.5 g of gum arabic, 0.15 g of dyestuff, 2 g of highly disperse silicon dioxide, 25 g of talc and 53.35 g of sugar, and dried. The resulting dragees each weigh 160.5 mg and each contain 0.5 mg of active substance.

c. 5.0 G of N,N-dimethyl-6-phenyl-8-chloro-4H-s-triazolo[4,3-a][1,4]benzodiazepine-1-carboxamide and 1,995 g of finely ground suppository base composition (for example cacao butter) are thoroughly mixed and then melted. 1,000 Suppositories weighing 2 g are cast from the melt, which is kept homogeneous by stirring. The suppositories each contain 5 mg of active substance.

The examples which follow explain in more detail the manufacture of the new compounds of the general formula I and of previously unknown starting substances but are not intended in any way to restrict the scope of the invention.

EXAMPLE 1

18 G (0.07 mol) of 2-azido-5-chlorobenzophenone are dissolved in 300 ml of absolute ethanol and 20 ml of pyridine and after addition of 29 g (0.24 mol) of 4-amino-2-butin-1-ol hydrochloride [J. Laroche and A. Marszak-Fleury, Compt. rend. 250, 1086–1087 (1960)] the mixture is boiled for 24 hours under reflux, whilst stirring. The reaction mixture is diluted with 500 ml of toluene, the insoluble salts are filtered off and the filtrate is evaporated in vacuo. The residue is dissolved in 200 ml of ethyl acetate and the solution is clarified by filtration using active charcoal and washed with 1 N hydrochloric acid until free of pyridine. After drying with sodium sulphate, 10 ml of 30% strength fluoboric acid are added to the ethyl acetate solution, whereupon the tetrafluoborate of the desired reaction product crystallises out. The process of separating out is completed by adding 200 ml of ether. The tetrafluoborate is filtered off, washed with ether and stirred with 200 ml of ethyl acetate and 100 ml of 5% strength sodium carbonate solution until a clear two-phase solution is obtained. The organic phase is separated off, washed with water until neutral and dried with sodium sulphate. After filtration and evaporation, a residue is obtained which when recrystallised from benzene-hexane gives 6-phenyl-8-chloro-4H-v-triazolo[1,5-a][1,4]benzodiazepine-3-methanol of melting point 183°–184°C.

2-Azido-5-chlorobenzophenone is prepared as follows:

a. 23.2 G (0.100 mol) of 2-amino-5-chloro-benzophenone [compare F. D. Chattaway, J. Chem. Soc. 85, 340 (1940)] are dissolved in 100 ml of glacial acetic acid and in 25 ml (0.3 mol) of 36% strength hydrochloric acid. 6.9 G (0.100 mol) of sodium nitrite dissolved in 25 ml of water are then added dropwise over the course of 15 minutes whilst stirring and cooling with water at 20°–25°C and 250 g of ice, 250 ml of water and 41.0 g (0.300 mol) of sodium acetate trihydrate are added to the solution. The turbid solution is clarified by filtration using charcoal and the filtrate is poured into a stirred solution of 16.2 g (0.250 mol) of sodium azide in 250 ml of glacial acetic acid. The resulting precipitate is filtered off, repeatedly washed with water and dried in vacuo over calcium chloride, after which 2-azido-5-chlorobenzophenone of melting point 81°–83°C is obtained.

EXAMPLE 2

0.054 G (0.001 mol) of ammonium chloride are dissolved in 1.65 g (0.030 mol) of 2-propinylamine at 25°C. 0.258 G (0.001 mol) of 2-azido-5-chloro-benzophenone [compare Example 1a] is added to this solution. The reaction mixture is boiled for 3 hours under reflux, cooled to 20°C and dissolved in 50 ml of benzene. The benzene solution is washed with 1 N hydrochloric acid and water until neutral, dried over sodium sulphate and evaporated in vacuo at 40°C. The residue is dissolved in 3 ml of isopropanol. 0.150 G (0.001 mol) of 70% strength aqueous perchloric acid in 2 ml of isopropanol is added to the isopropanol solution and the perchlorate is precipitated by adding 50 ml of ether, filtered off and washed with ether. The perchlorate, in 20 ml of methylene chloride, is then converted into the free base by means of 10 ml of ammonia. The methylene chloride solution is dried over potassium carbonate and evaporated in vacuo at 40°C. The residue is recrystallised from isopropanol, whereupon 6-phenyl-8-chloro-4H-v-triazolo[1,5-a][1,4]benzodiazepine of melting point 159°–162°C is obtained.

EXAMPLE 3

7.8 G (0.0283 mol) of 2-azido-5-chloro-2'-fluorobenzophenone are suspended in 120 ml of absolute ethanol and after addition of 8 ml of pyridine and 12 g (0.1 mol) of 4-amino-2-butin-1-ol hydrochloride [J. Laroche and A. Marszak-Fleury, Compt.rend. 250, 1086–1087 (1960)] the suspension is boiled for 24 hours under reflux, whilst stirring. The reaction mixture is diluted with 500 ml of toluene, the insoluble salts are filtered off and the filtrate is evaporated in vacuo. The residue is dissolved in ethyl acetate and the solution is washed first with water and then with 1 N hydrochloric acid and dried over sodium sulphate. The ethyl acetate solution is then chromatographed on a silica gel column and the column is eluted with ethyl acetate/methanol. The eluted product is recrystallised from benzene, whereupon 6-(o-fluorophenyl)-8-chloro-4H-v-triazolo[1,5-a][1,4]benzodiazepine-3-methanol of melting point 172°–173°C is obtained.

2-Azido-5-chloro-2'-fluorobenzophenone is prepared as follows:

a. 10 G (0.04 mol) of 2-amino-5-chloro-2'-fluorobenzophenone are dissolved in a mixture of 40 ml of glacial acetic acid and 10 ml of concentrated hydrochloric acid and diazotised with 10 ml (0.04 mol) of 4 M sodium nitrite solution. The mixture is then diluted with 200 ml of ice-cold water and neutralised by addition of 16.3 g (0.12 mol) of crystalline sodium acetate. The turbid solution is clarified by filtration using active charcoal and a solution of 8.5 g (0.13 mol) of sodium azide in 100 ml of water is then added. The reaction product which has precipitated is filtered off and washed with water until neutral. After drying over potassium hydroxide/calcium chloride in a desiccator, 2-azido-5-chloro-2'-fluorobenzophenone of decomposition point 90°C is obtained.

EXAMPLE 4

9.4 G (0.034 mol) of 2-azido-5-chloro-2'-fluorobenzophenone [see Example 3a] are dissolved in a solution of 100 ml of absolute ethanol and 80 ml of pyridine and after addition of 18.3 g (0.2 mol) of 2-propinylamine hydrochloride the mixture is boiled for 4 hours under reflux, while stirring. The reaction mixture is diluted with 500 ml of toluene, the insoluble salts are filtered off and the filtrate is evaporated in vacuo. The residue is dissolved in ethyl acetate and the solution is washed first with water and then with 1 N hydrochloric acid until free of pyridine, dried by means of sodium sulphate, filtered and evaporated in vacuo. The residue is dissolved in 30 ml of methylene chloride and 50 ml of ether and the reaction product is precipitated as the tetrafluoborate by addition of 30% strength aqueous fluoboric acid. The salt is filtered off, washed with ether on the filter and then decomposed with 2 N aqueous ammonia solution. The base liberated is taken up in methylene chloride and the solution is washed with water until neutral, dried with sodium sulphate and evaporated in vacuo. After recrystallisation from isopropanol, 6-(o-fluorophenyl)-8-chloro-4H-v-triazolo[1,5-a][1,4]benzodiazepine of melting point 194°–196°C is obtained.

EXAMPLE 5

5.8 G (0.02 mol) of 2-azido-5,2'-dichlorobenzophenone are dissolved in a mixture of 50 ml of absolute ethanol and 40 ml of pyridine and after addition of 9.15 g (0.1 mol) of 2-propinylamine hydrochloride the whole is boiled for 7 hours under reflux, whilst stirring. The reaction mixture is then diluted with 250 ml of toluene and the insoluble salts are filtered off. The filtrate is evaporated in vacuo. The residue is dissolved in ethyl acetate and the solution is washed first with water and then with 1 N hydrochloric acid until free of pyridine, dried with sodium sulphate, filtered and evaporated in vacuo. The residue is chromatographed on a silica gel column. Elution with benzene/ethyl acetate mixtures and subsequent recrystallisation from 80% strength ethanol gives 6-(o-chlorophenyl)-8-chloro-4H-v-triazolo[1,5-a][1,4]benzodiazepine of melting point 196°–198°C.

2-Azido-5,2'-dichlorobenzophenone is prepared as follows:

a. 6,65 G (0.025 mol) of 2-amino-5,2'-dichlorobenzophenone are dissolved in a mixture of 25 ml of glacial acetic acid and 6.25 ml of concentrated hydrochloric acid and diazotised with 5 ml (0.025 mol) of 5 M sodium nitrite solution at 20°C. The mixture is then diluted with 100 ml of ice-cold water and neutralised by addition of 10 g (0.075 mol) of crystalline sodium acetate, and the turbid solution is clarified by filtration, using active charcoal. A solution of 5 g (0.077 mol) of sodium azide in 50 ml of water is added to the filtrate. The reaction product which hereupon precipitates is filtered off and washed with water. After drying over potassium hydroxide and calcium chloride in a desiccator, 2-azido-5,2'-dichlorobenzophenone of decomposition point 100°C is obtained.

EXAMPLE 6

7.73 G (0.03 mol) of 2-azido-5-chlorobenzophenone [see Example 1a] are suspended in 75 ml of absolute ethanol and after addition of 7.6 g (0.09 mol) of 2-butine-1,4-diamine [A. Marszak-Fleury, Compt.rend. 241, 808 (1955)] and 1.6 g (0.03 mol) of ammonium chloride, the suspension is boiling for 24 hours under reflux, whilst stirring. The reaction mixture is then evaporated in vacuo and the residue is repeatedly worked into a paste with water and the liquid decanted. The water-insoluble residue is extracted three times with 100 ml of chloroform at a time and the combined extracts are dried with sodium sulphate and clarified by filtration using active charcoal. This chloroform solution is extracted three times with 100 ml of 0.2 N hydrochloric acid at a time, the combined acid extracts are rendered alkaline with 2 N aqueous ammonia solution and the bases which have precipitated are taken up in chloroform. The residue which remains after drying and evaporation of the chloroform solution is recrystallised twice from benzene/ether, whereupon, 3-(aminomethyl)-6-phenyl-8-chloro-4H-v-triazolo[1,5-a][1,4]benzodiazepine of melting point 164°–169°C is obtained.

EXAMPLE 7

A mixture of 5.15 g (0.02 mol) of 2-azido-5-chlorobenzophenone [see Example 1a], 50 ml of absolute ethanol, 6.7 g (0.06 mol) of N,N-dimethyl-2-butine-1,4-diamine [A. Marszak-Fleury, Ann. chim. (Paris) [13]3, 656-711 (1958)] and 1.07 g (0.02 mol) of ammonium chloride is boiled for 24 hours under reflux, while stirring. The reaction mixture is then evaporated in vacuo, the residue is dissolved in benzene and the benzene solution is repeatedly washed with water. The benzene solution is then extracted three times with 100 ml of 0.1 N hydrochloric acid at a time and the combined acid extracts are rendered alkaline with concentrated aqueous ammonia solution. The bases which precipitate are taken up in benzene and the solution is washed with water until neutral, dried with potassium carbonate, filtered and evaporated in vacuo. The residue is chromatographed on a column using basic aluminium oxide and eluting first with benzene/ethyl acetate and then with ethyl acetate. After recrystallisation, from cyclohexane-petroleum ether, of the ethyl acetate eluates which contain the desired product, 3-[(dimethylamino)-methyl]-6-phenyl-8-chloro-4H-v-triazolo[1,5-a][1,4]benzodiazepine of melting point 150°–152°C is obtained.

EXAMPLE 8

1.42 G (0.0044 mol) of 3-(aminomethyl)-6-phenyl-8-chloro-4H-v-triazolo[1,5-a][1,4]benzodiazepine [see Example 6] are dissolved in 90 ml of 0.1 N sulphuric acid and 11 ml (0.0044 mol) of 0.4 M aqueous sodium nitrite solution are added dropwise over the course of 2 hours at 20°–25°C. The reaction product which has precipitated is taken up in 100 ml of benzene and the solution is washed with water until neutral, dried with sodium sulphate, filtered and evaporated. The residue is crystallised from benzene/hexane and 6-phenyl-8-chloro-4H-v-triazolo[1,5-a][1,4]benzodiazepine-3-methanol of melting point 183°–184°C is obtained.

EXAMPLE 9

5.5 G of active manganese dioxide are added to a solution of 2 g (0.00615 mol) of 6-phenyl-8-chloro-4H-v-triazolo[1,5-a][1,4]benzodiazepine-3-methanol (see Example 1) in 200 ml of benzene and the mixture is boiled for 22 hours under reflux, whilst stirring. The reaction mixture is then filtered and the filtrate is evaporated in vacuo. The crude 6-phenyl-8-chloro-4H-s-triazolo[1,5-a][1,4]benzodiazepine-3-carboxaldehyde is converted further without additional purification. The active manganese dioxide is prepared according to J. Attenburrow et al., J.Chem.Soc. 1952, 1,104.

EXAMPLE 10

0.6 G (0.00175 mol) of 6-(o-fluorophenyl)-8-chloro-4H-v-triazolo[1,5-a][1,4]benzodiazepine-3-methanol [compare Example 3]are dissolved in 10 ml of hot benzene and after addition of 1.5 g of active manganese dioxide (J. Attenburrow et al., J.Chem.Soc. 1952, 1,104) the mixture is boiled for 2 hours under reflux, whilst stirring. The reaction mixture is filtered hot and the filtrate is evaporated in vacuo. The resulting crude 6-(o-fluorophenyl)-8-chloro-4H-v-triazolo[1,5-a][1,4]benzodiazepine-3-carboxaldehyde is converted further without purification.

EXAMPLE 11

1.61 G (0.005 mol) of 6-phenyl-8-chloro-4H-v-triazolo[1,5-a][1,4]benzodiazepine-3-carboxaldehyde [see Example 9] are dissolved in 200 ml of absolute methanol and 1.96 g (0.04 mol) of sodium cyanide are added. The mixture is stirred for 10 minutes at room temperature whereupon the sodium cyanide dissolved almost completely. 0.75 ml (0.013 mol) of acetic acid are then added, followed by 10 g (approx. 0.11 mol) of active manganese dioxide, and the suspension is stirred for 1 hour at 20°–25°C. It is then diluted with 200 ml of benzene and the inorganic material is filtered off. The filtrate is evaporated, the residue is dissolved in 100 ml of benzene and the solution is washed with ice-cold water until neutral. The benzene solution is dried with sodium sulphate and evaporated in vacuo. The residue is crystallised from 150 ml of methano and 6-phenyl-8-chloro-4H-v-triazolo[1,5-a][1,4]benzodiazepine-3-carboxylic acid methyl ester of melting point 205°–207°C is thus obtained.

EXAMPLE 12

1.76 G (0.005 mol) of 6-phenyl-8-chloro-4H-v-triazolo[1,5-a][1,4]benzodiazepine-3-carboxylic acid methyl ester (see Example 11) are dissolved in 300 ml of boiling methanol and 2 ml (0.02 mol) of 40% strength aqueous sodium hydroxide solution are added thereto. The mixture is boiled for one hour under reflux and is then evaporated in vacuo. The residue is dissolved in 200 ml of water at 60°C and the resulting carboxylic acid is precipitated by adding 30 ml of 1 N glycollic acid solution in water. The precipitate is filtered off, washed with water until neutral and recrystallised from isopropanol-water. 6-Phenyl-8-chloro-4H-v-triazolo[1,5-a][1,4]benzodiazepine-3-carboxylic acid, which decomposes at 178°C, is thus obtained.

EXAMPLE 13

3.38 G (0.01 mol) of 6-phenyl-8-chloro-4H-v-triazolo[1,5-a][1,4]benzodiazepine-3-carboxylic acid (see Example 12) and 34 ml of thionyl chloride are boiled for one hour under reflux. The clear yellow solution is evaporated in vacuo at 40°C and in order to remove the thionyl chloride completely the residue is again dissolved in 50 ml of absolute toluene and again evaporated.

The resulting crude mixture of 6-phenyl-8-chloro-4H-v-triazolo[1,5-a][1,4]benzodiazepine-3-carbonyl chloride and its hydrochloride is covered with a solution of 9 g (0.2 mol) of dimethylamine in 100 of absolute dioxane and left to stand for 1 hour at room temperature. The reaction mixture is then evaporated in vacuo at 40°C and the residue is dissolved in a mixture of 250 ml of chloroform and 100 ml of water. The organic phase is washed twice more with 100 ml of water at a time, dried over sodium sulphate and evaporated in vacuo at 40°C. The residue is crystallised from ethyl acetate and N,N-dimethyl-6-phenyl-8-chloro-4H-v-triazolo[1,5-a][1,4]benzodiazepine-3-carboxamide of melting point 208°–210°C is thus obtained.

EXAMPLE 14

3.53 G (0.01 mol) of 6-phenyl-8-chloro-4H-v-triazolo[1,5-a][1,4]benzodiazepine-3-carboxylic acid methyl ester (see Example 11) are suspended in 500 ml of methanol, 50 ml of 10% strength methanolic dimethylamine solution are added and the reaction mixture is stirred for 5 hours at room temperature. The clear solution is then evaporated in vacuo at 30°C and the residue is recrystallised from ethyl acetate, whereupon N,N-dimethyl-6-phenyl-8-chloro-4H-v-triazolo[1,5-a][1,4]benzodiazepine-3-carboxamide of melting point 208°–210°C is obtained.

EXAMPLE 15

1.47 G (0.03 mol) of sodium cyanide are suspended in 50 ml of isopropanol and 25 ml of a 20% strength solution of dimethylamine in dioxane are added at 0°–5°C. A solution of 2 g (0.0062 mol) of 6-phenyl-8-chloro-4H-v-triazolo[1,5-a][1,4]benzodiazepine-3-carboxaldehyde in 25 ml of dioxane is rapidly added dropwise after 10 minutes, and after a further 10 minutes 10.4 g of active manganese dioxide are introduced in two portions. The mixture is stirred for a further 3 hours at 0°–5°C and is filtered, and the filtrate is evaporated in vacuo. The residue is chromatographed on a silica gel column, with elution with benzene/ethyl acetate mixtures. After recrystallisation of the eluate from ethyl acetate, N,N-dimethyl-6-phenyl-8-chloro-4H-v-triazolo[1,5-a][1,4]benzodiazepine-3-carboxamide of melting point 208°–210°C is obtained.

The starting material is prepared according to Example 9.

EXAMPLE 16

0.55 G (0.0016 mol) of 6-(o-fluorophenyl)-8-chloro-4H-v-triazolo[1,5-a][1,4]benzodiazepine-3-carboxaldehyde is dissolved in 7 ml of dioxane and added dropwise, whilst stirring, to an ice-cooled suspension which was obtained by bringing together 0.43 g (0.0088 mol) of sodium cyanide in 15 ml of isopropanol and 7.5 ml of 20% strength dimethylamine solution in dioxane. After 10 minutes, 3.2 of active manganese dioxide are added in 2 portions and the mixture is stirred for a further 4 hours whilst cooling with ice. The reaction mixture is then filtered and the filtrate is evaporated in vacuo. The residue is chromatographed on a silica gel column. After elution with benzene/ethyl acetate and recrystallisation of the eluate from ethyl acetate, N,N-dimethyl-6-(o-fluorophenyl)-8-chloro-4H-v-triazolo[1,5-a][1,4]benzodiazepine-3-carboxamide of melting point 183°–185°C is obtained.

The starting material is prepared according to Example 10.

EXAMPLE 17

A mixture of 11.9 g (0.040 mol) of 6-phenyl-8-chloro-5,6-dihydro-4H-v-triazolo[1,5-a][1,4]benzodiazepine, 100 ml of pyridine and 4.5 g (0.0405 mol) of selenium dioxide is boiled for 20 minutes under reflux. The pyridine is then distilled off in vacuo at a bath temperature of 60°C and the residue is taken up in 500 ml of benzene. The selenium suspended in the benzene solution is removed by filtration through charcoal and the filtrate is washed with 1 N hydrochloric acid and water, dried over sodium sulphate and chromatographed on a column of 300 g of silica gel (Merck, particle size 0.05–0.2 mm). The eluant used is benzene/ethyl acetate (9:1). The eluant is evaporated and the residue is recrytallised from isopropanol. 6-Phenyl-8-chloro-4H-v-triazolo[1,5-a][1,4]benzodiazepine of melting point 160°–162°C is obtained.

6-Phenyl-8-chloro-5,6-dihydro-4H-v-triazolo [1,5-a][1,4]benzodiazepine, used as the starting material, is prepared as follows:

a. 25.8 G (0.100 mol) of 2-azido-5-chlorobenzophenone [compare Example 1a] are dissolved in 500 ml of pyridine/ethanol (1:1). 14.0 G (0.200 mol) of hydroxylamine hydrochloride are added to the solution and the mixture is boiled for 5 hours under reflux and evaporated in vacuo at 60°C. The residue is taken up in 250 ml of methanol and the solution is poured into 250 ml of 2 N hydrochloric acid. The crude product which precipitates is filtered off, suspended in 250 ml of 75% strength methanol, again filtered off and dried in vacuo. 2-Azido-5-chloro-benzophenone-oxime of melting point 125°–132°C is obtained. A sample of the crude product is recrystallised from benzene/cyclohexane, after which the pure compound melts at 135°–137°C.

b. 21.3 G (0.150 mol) of acetylenedicarboxylic acid dimethyl ester are dissolved in 25 ml of absolute dioxane. This solution is warmed, whilst stirring, to 95°C in a bath which is at 105°–110°C and 27.3 g of the azide obtained according to (a) are added in portions over the course of 30 minutes. In the course thereof, the temperature of the reaction mixture rises to 120°C and the dioxane boils under reflux. When all the azide has been introduced, the bath is additionally warmed to 105°–110°C for 15 minutes, 200 ml of carbon tetrachloride are then added, the bath is removed and the reaction solution is treated with 100 ml of cyclohexane. The crude product crystallises out. The suspension is cooled to 0°C and filtered and the crude product is washed three times with 50 ml of carbon tetrachloride at a time and dried in vacuo. 1-[4-Chloro-2-(α-hydroxyimino-benzyl)-phenyl]-1H-v-triazole-4,5-dicarboxylic acid dimethyl ester of melting point 160°–163°C is obtained.

c. 41.5 G (0.100 mol) of the compound prepared according to (b) are dissolved in 1.5 liters of methanol. 85 ml (1.0 mol) of 36.5% strength hydrochloric acid and a suspension of 10 g of 5% strength palladium on charcoal in 500 ml of methanol are added to the above solution and the mixture is hydrogenated under normal pressure at 30°–35°C. After 3 hours, 95% of the calculated amount of hydrogen have been taken up. The catalyst is filtered off and the filtrate is concentrated in 500 ml in vacuo at 30°C. The concentrate is dissolved in 5 liters of ice-cold water and the turbid solution is clarified by filtration with charcoal. The acid aqueous solution is covered with 1 liter of benzene and rendered alkaline with 100 g (1.2 mols) of sodium bicarbonate whilst stirring and cooling with ice. After separating off the benzene solution, the aqueous phase is extracted with 500 ml of ether. The combined ether solutions and benzene solutions are dried over sodium sulphate and evaporated in vacuo at 40°C. The residue, crude 1-[4-chloro-2-(α-amino-benzyl)phenyl]-1H-v-triazole-4,5-dicarboxylic acid dimethyl ester, is cyclised at 120°–130°C in a vacuum of 3 mm pressure. 6-Phenyl-8-chloro-5,6-dihydro-4-oxo-4H-v-triazolo[1,5-a][1,4]benzodiazepine-3-carboxylic acid methyl ester of melting point 250°C, with decomposition, is obtained. After recrystallisation from dioxane/hexane, the compound melts at 257°C, with decomposition.

d. 14.0 G (0.038 mol) of the compound prepared according to (c) are dissolved in 380 ml of N,N-dimethylformamide. 50 Ml of 1 N sodium hydroxide solution are added thereto and the mixture is boiled for 30 minutes under reflux. Insoluble sodium salt precipitates and is dissolved by adding 100 ml of water. The reaction solution is rendered acid with 50 ml of 2 N hydrochloric acid and 200 ml of water are then added. The free crude acid crystallises out. The suspension is cooled to 0°C and the precipitate is filtered off and repeatedly washed with water and then with acetone. 6-Phenyl-8-chloro-5,6-dihydro-4-oxo-4H-v-triazolo[1,5-a][1,4]benzodiazepine-3-carboxylic acid of melting point 215°C, with decomposition, is obtained.

e. 23.8 G (0.067 mol) of the compound prepared according to (d) are dissolved in 238 ml (2 mols) of quinoline. 2 G (0.003 mol) of copper powder are added to the solution and the suspension is heated to 140°C whilst stirring and passing nitrogen over it. After 2 hours, the evolution of carbon dioxide has ceased. The copper powder is then filtered off and rinsed with 240 ml of dioxane, and the warm quinoline/dioxane solution is poured into 1.5 liters of 2 N hydrochloric acid. The resulting suspension is cooled in an ice bath and the green precipitate is filtered off, rinsed with water and recrystallised from dioxane/water. 6-Phenyl-8-chloro-5,6-dihydro-4H-v-triazolo[1,5-a][1,4]benzodiazepin-4-one of melting point 235°–237°C is obtained.

f. 3.0 G (0.080 mol) of lithium aluminium hydride are suspended in 300 ml of absolute ether and 6.2 g (0.020 mol) of the compound prepared according to (e) are added in 2 portions to the suspension, whilst stirring and cooling with ice. The light yellow suspension is boiled for 3 hours under reflux and the excess of the reducing agent is subsequently destroyed by adding 15 ml of 1 N sodium hydroxide solution dropwise, whilst cooling with ice. The reaction mixture is diluted with 300 ml of benzene, the voluminous aluminates are filtered off through Hyflo (purified diatomaceous earth) and the filtrate is evaporated in vacuo at a bath temperature of 50°C. The residue is recrystallised from isopropanol, whereupon 6-phenyl-8-chloro-5,6-dihydro-4H-v-triazolo[1,5-a][1,4]benzodiazepine of melting point 127°–129°C is obtained.

EXAMPLE 18 a. 5.94 G (0.020 mol) of 6-phenyl-8-chloro-5,6-dihydro-4H-v-triazolo[1,5-a][1,4]benzodiazepine [compare Example 17f] are dissolved in 60 ml of methylene chloride. 10.4 g (0.020 mol) of 85% strength lead tetraacetate, dissolved in 200 ml of methylene chloride, are added dropwise to this solution at 10°–20°C, whilst stirring. 5 Ml of water are then added, the mixture is stirred for a further 30 minutes, and the resulting precipitate is filtered off through Hyflo (purified diatomaceous earth). The clear filtrate is washed with 5% strength sodium bicarbonate solution, dried over sodium sulphate and evaporated in vacuo at 40°C. The residue (5.6 g) contains a crude isomer mixture of 6-phenyl-8-chloro-4H- and 6-phenyl-8-chloro-6H-v-triazolo[1,5-a][1,4]benzodiazepine which is converted, in accordance with the subsequent sections b–c or d), into pure 6-phenyl-8-chloro-4H-v-triazolo[1,5-a][1,4]benzodiazepine.

b. The isomer mixture obtained according to (a) (5.6 g) is dissolved in 100 ml of absolute benzene, the benzene solution is passed over a column of 250 g of silica gel (Merck, particle size 0.05–0.2 mm) and the column is eluted with benzene/ethyl acetate (19:1). The eluate is evaporated in vacuo at 60°C and the residue is re-crystallised frm isopropanol, whereupon 6-phenyl-8-chloro-6H-v-triazolo[1,5-a][1,4]benzodiazepine of melting point 127°–130°C is obtained.

c. 2.95 G (0.010 mol) of the compound obtained according to (b) are dissolved in 100 ml of toluene. 0.124 g (0.001 mol) of 1,5-diazabicyclo[4.3.0]non-5-ene is added to this solution and the mixture is boiled for 3 hours under reflux and cooled. The reaction solution is then washed with 12 ml of 0.1 N hydrochloric acid and with 50 ml of water, dried over sodium sulphate and evaporated in vacuo at 50°C. After recrystallisation of the residue from isopropanol, pure 6-phenyl- 8-chloro-4H-v-triazolo[1,5-a][1,4]benzodiazepine of melting point 160°–162°C is obtained.

d. 2.95 G (0.010 mol) of the isomer mixture obtained according to (a) are dissolved in 100 ml. of toluene. 0.124 g (0.001 mol) of 1,5-diazabicyclo[4.3.0]non-5-ene is added to this solution and the mixture is boiled for 3 hours under reflux. The reaction solution is then cooled to 20°C, washed with 12 ml of 0.1 N hydrochloric acid and 50 ml of water, dried over sodium sulphate and evaporated in vacuo at 50°C. Recrystallisation of the resulting residue from isopropanol yields 6-phenyl-8-chloro-4H-v-triazolo[1,5-a][1,4]benzodiazepine of melting point 159°–162°C.

EXAMPLE 19

2.97 G (0.010 mol) of 6-phenyl-8-chloro-5,6-dihydro-4H-v-triazolo[1,5-a][1,4]benzodiazepine [compare Example 17f] are dissolved in 30 ml of 95 % strength acetic acid and 1.0 g (0.00335 mol) of sodium dichromate dihydrate in 5 ml of water are added dropwise to this solution at 50°–60°C, whilst stirring. The reaction mixture is stirred for a further 15 minutes at the same temperature and is then diluted with 200 ml of water. The resulting green suspension is twice extracted with 100 ml of benzene at a time and the benzene extract is washed with water and 5% strength sodium bicarbonate solution until neutral, dried over sodium sulphate, decolorised with charcoal and evaporated in vacuo at 50°C. A crude mixture of 6-phenyl-8-chloro-4H- and 6-phenyl-8-chloro-6H-v-triazolo[1,5-a][1,4]benzodiazepine is obtained, which is converted in accordance with Example 18d into pure 6-phenyl-8-chloro-4H-v-triazolo[1,5-a][1,4]benzodiazepine of melting point 159°–162°C.

EXAMPLE 20 a. 2.97 G (0.010 mol) of 6-phenyl-8-chloro-5,6-dihydro-4H-v-triazolo[1,5-a][1,4]benzodiazepine prepared according to Example 17f are dissolved in 200 ml of benzene. 10.5 g (0.100 mol) of active manganese dioxide (compare J. Attenburrow et al., J.Chem.Soc. 1952, 1,104) are added to this solution, whilst stirring, the mixture is boiled under reflux and the resulting water is distilled of azeotropically. The reaction mixture is cooled to 20°C and filtered, and the filtrate is evaporated in vacuo at 50°C, after which a crystalline crude mixture of 6-phenyl-8-chloro-4H- and 6-phenyl-8-chloro-6H-v-triazolo[1,5-a][1,4]benzodiazepine is obtained.

b. 2.95 G (0.010 mol) of the mixture obtained according to (a) are dissolved in 100 ml of toluene and 10 ml of absolute ethanol. 0.056 G (0.005 mol) of potassium tert.butylate are added to this solution and the mixture is boiled for 10 minutes under reflux and cooled to 20°C. The reaction solution is washed with water, dried over sodium sulphate and evaporated in vacuo at 50°C. The residue is recrystallised from isopropanol and 6-phenyl-8-chloro-4H-v-triazolo[1,5-a][1,4]benzodiazepine of melting point 158°–162°C are obtained

EXAMPLE 21

14.7 G (0.050 mol) of 6-phenyl-8-chloro-4H-v-triazolo[1,5-a][1,4]benzodiazepine are dissolved in 500 ml of methylene chloride. 10.2 G (0.050 mol) of 85% strength m-chloroperoxybenzoic acid are added to this solution at 25°C and the mixture is left to stand for 24 hours at 20°–25°C. The reaction solution is then washed with 5% strength sodium bicarbonate solution, dried over sodium sulphate and evaporated in vacuo at 40°C. The residue is dissolved in 200 ml of benzene/ethyl acetate (9:1) and is chromatographed on a column of 400 g of basic aluminium oxide (Woelm, activity level 1). The column is eluted with benzene/ethyl acetate (9:1) and the resulting fractions are evaporated. The first fractions contain unchanged starting compound and the following fractions contain the crude end product. This is recrystallised from isopropanol, whereupon 6-phenyl-8-chloro-4H-v-triazolo[1,5-a][1,4]benzodiazepine-5-oxide of melting point 228°–230°C is obtained.

EXAMPLE 22

22.8 G (0.12 mol) of titanium tetrachloride are added dropwise to 150 ml of absolute pyridine at 0–10°C. The suspension is allowed to warm to room temperature and 3.66 g (0.04 mol) of propargylamine hydrochloride and 5.36 g (0.02 mol) of 2-azido-5-nitro-benzophenone are subsequently added. The reaction mixture is stirred for 48 hours at 25°–30°C and is then poured onto a mixture of 500 g of ice and 170 ml of concentrated hydrochloric acid and extracted 3 times with 200 ml of methylene chloride at a time. The combined extracts are washed first with 1 N hydrochloric acid and then with water, dried over sodium sulphate and evaporated in vacuo at 30°C. The residue is dissolved in 100 ml of ethyl acetate, the solution is clarified by filtration using active charcoal, and 4 ml of 30% strength aqueous fluoboric acid are then added. The tetrafluoborate which crystallises out is filtered off and washed with ether.

The tetrafluoborate, in 50 ml of methylene chloride, is then converted into the free base with 50 ml of 5 N ammonia. The methylene chloride solution is dried with sodium sulphate and evaporated in vacuo. For further purification, the residue is crystallised from ethyl acetate and 6-phenyl-8-nitro-4H-v-triazolo[1,5-a][1,4]benzodiazepine of melting point 204°–207°C is thus obtained.

The starting material is manufactured as follows:

a. 4.84 g (0.02 mol) of 2-amino-5-nitro-benzophenone (Ullmann Ber. 31, 1965) are dissolved in 100 ml of glacial acetic acid and 5 ml of concentrated hydrochlorid acid are then added. The solution is diazotised at 20°–25°C with 4 ml of 5 N aqueous sodium nitrite solution and is subsequently diluted with 100 ml of ice water. The solution is buffered to pH 4–5 by addition of sodium acetate; a solution of 3.25 g (0.05 mol) of sodium azide in 20 ml of water is then poured in, whereupon the azide precipitates as a yellow smeary product. The product is dissolved in 100 ml of benzene and the solution is washed with dilute sodium bicarbonate solution until free of acid. After drying over sodium sulphate, the solution is evaporated and the residue is crystallized from benzene-cyclohexene at a temperature not exceeding 60°C, whereupon 2-azido-5-nitro-benzophenone is obtained as yellow crystals of melting point 97°–100°C (with decomposition).

EXAMPLE 23

2.92 G (0.01 mol) of 2-azido-5,2'-dichloro-benzophenone (see Example 5a) are dissolved in 75 ml of absolute pyridine and 3.6 g (0.03 mol) of 4-amino-2-butin-1-ol hydrochloride are suspended in this solution. 11.4 G (0.06 mol) of titanium tetrachloride are now added dropwise over the course of 15 minutes whilst stirring at −10° to 0°C and the mixture is then stirred in the dark for 4 days at room temperature. The black reaction mixture is then introduced into an ice-cooled mixture of 500 ml of 2 N hydrochloric acid and 500 ml of ethyl acetate. The organic phase is washed with water until neutral, dried with sodium sulphate and evaporated in vacuo. The residue is chromatographed on a silica gel column and the column is eluted with benzene with increasing proportions of ethyl acetate. The eluted product is recrystallised from ether, whereupon 6-(o-chlorophenyl)-8-chloro-4H-v-triazolo[1,5-a][1,4]benzodiazepine-3-methanol of melting point 144°–148°C is obtained.

EXAMPLE 24

Analogously to Example 9, 0.5 g (0.0014 mol) of 6-(o-chlorophenyl)-8-chloro-4H-v-triazolo[1,5-a][1,4]benzodiazepine-3-methanol are dissolved in 50 ml of methylene chloride and 50 ml of benzene and after the addition of 5 g of active manganese dioxide the mixture is stirred at room temperature, the reaction being followed by means of thin layer chromatography. After 2 hours, the starting material has been oxidised; the reaction mixture is then filtered and the filtrate is evaporated in vacuo, whereupon 6-(o-chlorophenyl)-8-chloro-4H-v-triazolo[1,5-a][1,4]benzodiazepine-3-carboxaldehyde is obtained as a crude product.

EXAMPLE 25

Analogously to Example 16, 0.465 g (0.0013 mol) of 6-(o-chlorophenyl)-8-chloro-4H-v-triazolo[1,5-a][1,4]benzodiazepine-3-carboxaldehyde are reacted with 500 mg of sodium cyanide, 10 ml of 20% strength dimethylamine solution in absolute dioxane and 5 g of active manganese dioxide for 3 hours at 20°–25°C. After chromatography on a silica gel column and recrystallisation from ether, N,N-dimethyl-6-(o-chlorophenyl)-8-chloro-4H-v-triazolo [1,5-a][1,4]benzodiazepine-3-carboxamide of melting point 178°–180°C is obtained.

What we claim is:

1. A new diazepine derivative of formula I

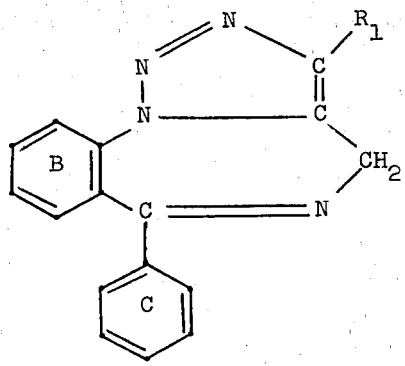

in which $R_1$ represents hydrogen, hydroxymethyl, formyl, carboxy, lower alkoxycarbonyl, or a group of formula Ia

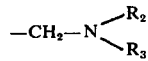

in which $R_2$ and $R_3$ independently of each other represent hydrogen or lower alkyl, or a group of formula Ib

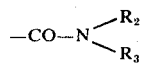

in which $R_2$ and $R_3$ have the meanings defined above, ring B is unsubstituted or substituted in the 8-position by halogen up to atomic number 35, trifluoromethyl or nitro, and ring C is unsubstituted or substituted by one substituent of the group of halogen atoms up to atomic number 35, trifluoromethyl and nitro, and its 5-oxide and its pharmaceutically acceptable addition salts with inorganic and organic acids.

2. A compound according to claim 1, in which $R_1$ is hydrogen, hydroxymethyl, formyl, carboxy, lower alkoxycarbonyl or a group of formula Ia, in which $R_2$ and $R_3$ independently of each other represent hydrogen, methyl or ethyl, or a group of formula Ib, in which $R_2$ and $R_3$ have the meanings defined above, ring B is unsubstituted or substituted in the 8-position by halogen up to atomic number 35, trifluoromethyl or nitro, and ring C is unsubstituted or substituted by one substituent of the group of halogen up to atomic number 35, trifluoromethyl or nitro.

3. A compound according to claim 1, in which $R_1$ is hydrogen, hydroxymethyl, formyl, carboxy, lower alkoxycarbonyl or a group of formula Ia, in which $R_2$ and $R_3$ independently of each other represent hydrogen, methyl or ethyl, or a group of formula Ib, in which $R_2$ and $R_3$ have the meanings defined above, ring B is substituted in the 8-position by chlorine or nitro and ring C is unsubstituted or substituted in the o-position by fluorine or chlorine.

4. A compound according to claim 1, in which $R_1$ is hydroxymethyl, formyl, carboxyl, or lower alkoxycarbonyl, ring B is substituted in the 8-position by chlorine or nitro and ring C is unsubstituted or substituted in the o-position by fluorine or chlorine.

5. A compound according to claim 1, in which $R_1$ is hydrogen or a group of formula Ib, in which $R_2$ and $R_3$ independently of each other represent hydrogen, methyl or ethyl, ring B is substituted in the 8-position by chlorine or nitro and ring C is unsubstituted or substituted in the o-position by fluorine or chlorine.

6. A compound according to claim 1, which is 6-phenyl-8-chloro-4H-v-triazolo[1,5-a][1,4]benzodiazepine-3-methanol.

7. A compound according to claim 1, which is 6-(o-fluorophenyl)-8-chloro-4H-v-triazolo[1,5-a][1,4]benzodiazepine-3-methanol.

8. A compound according to claim 1, which is 6-(o-chlorophenyl)-8-chloro-4H-v-triazolo[1,5-a][1,4]benzodiazepine-3-methanol.

9. A compound according to claim 1, which is 6-phenyl-8-chloro-4H-v-triazolo[1,5-a][1,4]benzodiazepine-3-carboxaldehyde.

10. A compound according to claim 1, which is 6-(o-fluorophenyl)-8-chloro-4H-v-triazolo[1,5-a][1,4]benzodiazepine-3-carboxaldehyde.

11. A compound according to claim 1, which is 6-(o-chlorophenyl)-8-chloro-4H-v-triazolo[1,5-a][1,4]benzodiazepine-3-carboxaldehyde.

12. A compound according to claim 1, which is 6-phenyl-8-chloro-4H-v-triazolo1,5-a1,4]benzodiazepine-3-carboxylic acid.

13. A compound according to claim 1, which is 6-phenyl-8-chloro-4H-v-triazolo-[1,5-a][1,4benzodiazepine-3-carboxylic acid methyl ester.

14. A compound according to claim 1, which is 3-(aminomethyl)-6-phenyl-8-chloro-4H-v-triazolo[1,5-a][1,4]benzodiazepine.

15. A compound according to claim 1, which is 3-[(dimethylamino)-methyl]-6-phenyl-8-chloro-4H-v-triazolo[1,5-a][1,4]benzodiazepine.

16. A compound according to claim 1, which is 6-phenyl-8-chloro-4H-v-triazolo[1,5-a][1,4]benzodiazepine.

17. A compound according to claim 1, which is 6-(o-fluorophenyl)-8-chloro-4H-v-triazolo[1,5-a][1,4]benzodiazepine.

18. A compound according to claim 1, which is 6-(o-chlorophenyl)-8-chloro-4H-v-triazolo[1,5-a][1,4]benzodiazepine.

19. A compound according to claim 1, which is 6-phenyl-8-nitro-4H-v-triazolo[1,5-a][1,4]benzodiazepine.

20. A compound according to claim 1, which is 6-phenyl-8-chloro-4H-v-triazolo[1,5-a][1,4]benzodiazepine-5-oxide.

21. A compound according to claim 1, which is N,N-dimethyl-6-phenyl-8-chloro-4H-v-triazolo[1,5-a][1,4]benzodiazepine-3-carboxamide.

22. A compound according to claim 1, which is N,N-dimethyl-6-(o-fluorophenyl)-8-chloro-4H-v-triazolo[1,5-a][1,4]benzodiazepine-3-carboxamide.

23. A compound according to claim 1, which is N,N-dimethyl-6-(o-chlorophenyl)-8-chloro-4H-v-triazolo[1,5-a][1,4]benzodiazepine-3-carboxamide.

* * * * *